(12) United States Patent
Yahiaoui et al.

(10) Patent No.: US 7,816,412 B2
(45) Date of Patent: Oct. 19, 2010

(54) ELECTRICALLY CONDUCTIVE HYDROGELS

(75) Inventors: Ali Yahiaoui, Roswell, GA (US); Anthony Stephen Spencer, Woodstock, GA (US); Charles Bolian, Buford, GA (US)

(73) Assignee: ConMed Corporation, Utica, NY (US)

( * ) Notice: Subject to any disclaimer, the term of this patent is extended or adjusted under 35 U.S.C. 154(b) by 628 days.

(21) Appl. No.: 11/709,996

(22) Filed: Feb. 23, 2007

(65) Prior Publication Data

US 2008/0207779 A1 Aug. 28, 2008

(51) Int. Cl.
*A61K 9/107* (2006.01)
*A61P 17/16* (2006.01)
*A61L 24/00* (2006.01)

(52) U.S. Cl. .......................... 516/99; 424/486; 523/111
(58) Field of Classification Search ........................ None
See application file for complete search history.

(56) References Cited

U.S. PATENT DOCUMENTS

| | | | |
|---|---|---|---|
| 3,736,306 A | 5/1973 | Light | |
| 3,845,757 A | 11/1974 | Weyer | |
| 3,911,906 A | 10/1975 | Reinhold, Jr. | |
| 4,242,242 A | 12/1980 | Allen | |
| 4,391,278 A | 7/1983 | Cahalan et al. | |
| 4,524,087 A | 6/1985 | Engel | |
| 4,539,996 A | 9/1985 | Engel | |
| 4,554,924 A | 11/1985 | Engel | |
| 4,581,821 A | 4/1986 | Cahalan et al. | |
| 4,702,732 A | 10/1987 | Powers et al. | |
| 4,842,768 A | 6/1989 | Nakao et al. | |
| 4,848,353 A | 7/1989 | Engel | |
| 4,909,244 A | 3/1990 | Quarfoot et al. | |
| 5,050,099 A | 9/1991 | Nishihara et al. | |
| 5,124,076 A | 6/1992 | Smuckler | |
| 5,183,599 A | 2/1993 | Smuckler | |
| 5,264,249 A | 11/1993 | Perrault et al. | |
| 5,338,490 A | 8/1994 | Dietz et al. | |
| 5,402,884 A | 4/1995 | Gilman et al. | |
| 5,480,717 A | 1/1996 | Kundel | |
| 5,536,446 A | 7/1996 | Uy et al. | |
| 5,660,178 A | 8/1997 | Kantner et al. | |
| 5,674,275 A | 10/1997 | Tang et al. | |
| 5,800,685 A | 9/1998 | Perrault | |
| 6,038,464 A | 3/2000 | Axelgaard et al. | |
| 6,121,508 A | 9/2000 | Bischof et al. | |
| 6,174,929 B1 | 1/2001 | Hahnle et al. | |
| 6,197,173 B1 | 3/2001 | Kirkpatrick | |
| 6,198,955 B1 | 3/2001 | Axelgaard et al. | |
| 6,229,062 B1 | 5/2001 | Mandell et al. | |
| 6,232,366 B1 | 5/2001 | Wang et al. | |
| 6,272,385 B1 | 8/2001 | Bishay et al. | |
| 6,344,218 B1 | 2/2002 | Dodd et al. | |
| 6,347,246 B1 | 2/2002 | Perrault et al. | |
| 6,372,815 B1 | 4/2002 | Sulc et al. | |
| 6,418,342 B1 | 7/2002 | Owen et al. | |
| 6,546,285 B1 | 4/2003 | Owen et al. | |
| 6,559,223 B2 | 5/2003 | Green et al. | |
| 6,602,952 B1 | 8/2003 | Bentley et al. | |
| 6,656,456 B2 | 12/2003 | Dodd et al. | |
| 6,673,852 B1 | 1/2004 | Suda et al. | |
| 6,767,632 B2 | 7/2004 | Axelgaard et al. | |
| 6,792,301 B2 | 9/2004 | Munro et al. | |
| 6,842,636 B2 | 1/2005 | Perrault et al. | |
| 7,045,559 B2 | 5/2006 | Yahiaoui et al. | |
| 2002/0026005 A1 | 2/2002 | Munro | |
| 2003/0031715 A1 | 2/2003 | Park et al. | |
| 2003/0054024 A1 | 3/2003 | Munro et al. | |
| 2004/0057986 A1 | 3/2004 | Merrigan et al. | |
| 2005/0136023 A1 | 6/2005 | Yahiaoui et al. | |
| 2005/0136077 A1 | 6/2005 | Yahiaoui et al. | |
| 2006/0258788 A1 | 11/2006 | Coggins et al. | |

FOREIGN PATENT DOCUMENTS

| | | |
|---|---|---|
| DE | 19911260 | 9/2000 |
| EP | 1245241 | 10/2002 |
| EP | 1358894 | 11/2003 |
| JP | 2002035141 | 2/2002 |
| WO | WO-9731971 | 9/1997 |
| WO | WO-98/19311 | 5/1998 |
| WO | WO-00/14131 | 3/2000 |
| WO | WO-00/45864 | 8/2000 |

(Continued)

OTHER PUBLICATIONS

McAdams, E., "Surface Biomedical Electrode Technology", *International Medical Device & Diagnostic Industry*, Sep./Oct. 1990, pp. 44-48.

(Continued)

*Primary Examiner*—Shanon A Foley
(74) *Attorney, Agent, or Firm*—Timothy D Evans

(57) ABSTRACT

Electrically conductive adhesive hydrogels formed from a composition which generally includes a monomer, an initiator, an organic solvent, and a cross-linking agent are suitable for use as skin contact adhesives and, particularly, suitable for use as an electrical interface for disposable medical devices. The present hydrogels provide for reduced skin irritation and/or malodor properties, hydrate a subject's skin, readily wet around a subject's skin surface hair, and protect against burning of a subject upon or due to electrical stimulation through the hydrogel.

32 Claims, No Drawings

FOREIGN PATENT DOCUMENTS

| WO | WO-00/66187 | 11/2000 |
|---|---|---|
| WO | WO-01/56649 | 8/2001 |
| WO | WO 03/051408 | 6/2003 |
| WO | WO-03/051408 | 6/2003 |
| WO | WO-03/089506 | 10/2003 |
| WO | WO-2004/029169 | 4/2004 |
| WO | WO 2004/052415 | 6/2004 |
| WO | WO-2004/052415 | 6/2004 |
| WO | WO-2005/061017 | 7/2005 |
| WO | WO 2005/079878 | 9/2005 |

OTHER PUBLICATIONS

International Search Report and Written Opinion of the International Searching Authority for PCT/US2008/053709 mailed Jul. 7, 2008 (11 pgs.).

McADAMS, E., "Surface Biomedical Electrode Technology", *International Medical Device & Diagnostic Industry*, Sep./Oct. 1990, pp. 44-48.

Berner, G. et al., "Photoinitiators-An Overview", *Journal of Radiation Curing*, Apr. 1979, pp. 2-9.

Liu, Yuyang et al., "Synthesis and characterization of pH- and temperature-sensitive hydrogel of N-isopropylacrylamide/cyclodextrin based copolymer", *Polymer*, vol. 43, No. 18, Aug. 2002, pp. 4997-5003.

Derwent-Acc-No. 1993-285460k Jan. 28, 1992. (3 pgs.).

Materials Safety Data Sheet, 2-Hydroxyethyl Methacrylate Stblzd w 250ppm MEHQ MSDS, viewed and printed from the web Dec. 8, 2006. (6 pgs.).

Tracy et al., "Radioimmunoassay for Methotrexate Using Hydroxyethylmethacrylate Hydrogel," *Cancer Chemotherapy and Pharmacology*, 1983, pp. 96-99.

Delvalle, Martin, E.M., "Cyclodextrins and their uses: a review", *Science Direct*, 2004, pp. 1033-1046.

ELECTRICALLY CONDUCTIVE HYDROGELS

BACKGROUND

At present, electrically conductive adhesive solid hydrogels and liquid gels are used in the medical device field to provide an electrical interface to the skin of a subject to couple electrical signals into and/or out of the subject (e.g., for diagnostic and/or monitoring uses) and/or to couple electrical stimulus into the subject (e.g., for treatment and/or preventative uses). However, the present hydrogels and liquid gels are inadequate in various aspects.

Prior hydrogels exhibit problems with their adhesive and/or cohesive strength in that they do not sufficiently adhere to the skin, they are insufficiently cohesive to allow for easy removal, and/or they are adherent to themselves such that they must be physically separated, as by a barrier film, to ensure separability (no straight face-to-face, gel-to-gel, configurations). See, e.g., Gilman, et al., U.S. Pat. No. 5,402,884 (a package system providing electrical communication between two hydrogel portions, but still requiring separation of the two hydrogel portions). Additional problems with prior hydrogels concern sufficiently hydrating the skin in contact with the hydrogel and, therefore, problems with sufficiently lowering the skin's electrical resistance thereby frequently resulting in heating to a point of burning the skin upon electrical stimulation. See, e.g., E. McAdams, "Surface Biomedical Electrode Technology," Int'l Med. Device & Diagnostic Indus. pp. 44 48 (September/October 1990).

Further problems with prior hydrogels include insufficiently wetting around skin hair and resultant problems with insufficiently contacting the skin. This leads to insufficient electrical contact thereby frequently resulting in decreased efficacy of defibrillation and increased incidences of heating to the point of burning the skin upon electrical stimulation and/or problems of requiring preparation of skin surfaces prior to use thereby resulting in slowing the speed of procedures. Further still, electrical pulses transmitted through prior hydrogels to a patient cause hydrolysis of the gel, and this problem is exacerbated with medical stimulation equipment used for defibrillation and/or cardiac pacing because these types of stimulation equipment usually deliver higher voltages and currents to the patient which increases the rate of hydrolysis. For example, defibrillation equipment typically delivers up to 5,000 volts to the patient at a maximum current of 60 amps, and cardiac pacing equipment commonly delivers up to 300 volts to the patient at a maximum current of 0.2 amps.

Yet another problem with prior hydrogels is that the hydrogels often have an unpleasant odor associated with them and are irritating to the skin of a patient. Skin irritation issues and odor often arise where polymerization of the functional monomer and/or other monomeric residues in the hydrogel is not complete. In some cases, other undesired monomeric or other residues are present and, over time after manufacture, may come in direct contact with the patient skin and thus may further cause skin irritation or cause malodor.

Prior hydrogels have attempted to overcome this unpleasant odor and irritation of the skin (caused by lack of polymerization of the monomer) by introducing a solubilizer to enhance the solubility of a polymerization initiator. Although effective, solubilizers are very expensive and are often up to 35 times as expensive as a comparable amount of organic solvent.

Thus, there remains a need to develop a cost effective hydrogel which is not malodorous and does not irritate the skin, while still providing properties of adhesive and cohesive strength and sufficient wetting.

SUMMARY

The present invention provides for an electrically conductive hydrogel formed from a composition including a monomer, at least one initiator, a cross-linking agent, and an organic solvent. The pH of the hydrogel may be maintained in the range of 3 to 8.5 in the absence of a dual buffer system. An acidic salt or the acid form of a monomer may be used to maintain the pH of the hydrogel in the range of 3 to 8.5. The hydrogel may be formed from a composition that does not include a solubilizer for the at least one initiator. Desirably, the organic solvent is dimethyl sulfoxide and is between about 0.5% and about 5% by weight of the composition. Additionally, the composition may include a buffer.

The monomer of the composition is desirably N,N-Dimethylaminoethyl acrylate dimethyl sulfate quaternary, dimethyl amino ethyl methacrylate, acrylamido methyl propane sulfonic acid or their salts. The monomer desirably is about 10% to about 80% by weight of the composition and is more desirably about 40% to about 75% by weight of the composition.

The cross-linking agent is about 0.01% to about 2% by weight of the composition and the initiator comprises about 0.01% to about 2% by weight of the composition. Desirably, the initiator is a chemical initiator, a photo initiator, or both. When the initiator is a chemical initiator, it may be thermally activated and may be disulfide based, peroxide based, or persulfate based or may be a sodium metabisulfite. Additionally, the initiator may be a hydrophobic initiator.

Additionally, the composition may desirably include skin health agent, which reduces irritation to the skin, particularly irritation caused by the use of dimethyl sulfoxide as an organic solvent. These skin health agents include aloe vera, glycerin, vitamin E, vitamin B, provitamin B, vitamin E acetate, or chitosan.

Another aspect of the invention addresses an electrode which includes an electrically conductive adhesive hydrogel formed from a composition. The composition includes a monomer, at least one initiator, a cross-linking agent, and an organic solvent. The pH of the hydrogel may be maintained in the range of 3 to 8.5 in the absence of a dual buffer system. Desirably, the composition may further include a skin health agent which may include an electrically conductive hypoallergenic layer which is in communication with the electrically conductive hydrogel.

Yet another aspect of the invention addresses a composition for an electrically conductive hydrogel. The hydrogel includes at least one monomer, at least one initiator, a cross-linking agent, and an organic solvent. The pH of the hydrogel may be maintained in the range of 3 to 8.5 in the absence of a dual buffer system.

Definitions

Solubilizer—An agent that increases the amount of a substance that will dissolve in a given amount of another substance. For example, a particular amount of a hydrophilic substance may dissolve in water, but the use of a solubilizer, i.e. cyclodextrin, will increase the amount of the hydrophilic substance that may be dissolved in water.

Solvent—A substance capable of dissolving another substance (solute) to form a uniformly dispersed mixture (solution) at the molecular or ionic size level. Solvents are either polar (high dielectric constant) or non-polar (low dielectric constant). Water, the most common of all solvents, is strongly polar (dielectric constant 81), but hydrocarbon solvents are non-polar. Aromatic hydrocarbons have higher solvent power than aliphatics (alcohols). Other organic solvent groups are esters, ethers, ketones, amines and nitrated and chlorinated hydrocarbons.

DETAILED DESCRIPTION

The invention disclosed herein is directed to electrically conductive hydrogels. The hydrogels include a monomer, initiator, cross-linking agent, and an organic solvent. The hydrogels are electrically conductive adhesive hydrogels which are good electrical conductors suitable for use in disposable medical devices, for example. These hydrogels are desirably non-irritating to the skin, are sufficiently wet to adhere to skin, and are readily removable from skin when desired. The organic solvent of the hydrogel acts as a solvent for the initiator and provides a significant cost savings over the use of a solubilizer for the initiator.

It will be appreciated that while reference is generally made throughout this disclosure to a hydrogel, in addition to referring to the end product, the term hydrogel, also may refer to the polymerizing formulation or hydrogel precursor which is converted to a hydrogel upon exposure to certain conditions (e.g., ultraviolet or UV curing, heat, etc.) as discussed elsewhere herein.

The invention will be described with reference to the following description and figures which illustrate certain embodiments. It will be apparent to those skilled in the art that these embodiments do not represent the full scope of the invention which is broadly applicable in the form of variations and equivalents as may be embraced by the claims appended hereto. Furthermore, features described or illustrated as part of one embodiment may be used with another embodiment to yield still a further embodiment. It is intended that the scope of the claims extend to all such variations and embodiments.

In the interests of brevity and conciseness, any ranges of values set forth in this specification contemplate all values within the range and are to be construed as support for claims reciting any sub-ranges having endpoints which are whole number values within the specified range in question. By way of a hypothetical illustrative example, a disclosure in this specification of a range of from 1 to 5 shall be considered to support claims to any of the following ranges: 1-5; 14; 1-3; 1-2; 2-5; 2-4; 2-3; 3-5; 34; and 4-5.

Compared to conventional conductive hydrogel formulations, the hydrogels of the present invention exhibit enhanced polymerization as evidenced by clear or substantially clear gel solutions, the absence of precipitates or presence of only limited precipitates, generally high electrical conductivity values, and are characterized by the absence of solubilizers for the initiator. Thus, the amount of undesirable residual functional monomer and/or other monomeric residues in the hydrogel which are unpolymerized is reduced. The present hydrogels exhibit these enhanced polymerization and electrically conductive properties without the need for expensive solubilizers for the initiator.

An additional advantage of the hydrogels of the present invention is that they may utilize an electrolyte or combination of electrolytes as conductivity enhancers.

Clear gel solutions of the present inventions are demonstrated when there is no residue or precipitates visible in the formulation with the naked or unaided eye. Substantially clear gel solutions are demonstrated by either an amount of residue or precipitate in the solution that does not cause the solution to demonstrate unsatisfactory conductivity values. Generally speaking, satisfactory electrical conductivity values are values ranging from about 30 mS/cm to about 50 mS/cm.

With regard to the functional monomer, it is contemplated that the hydrogels may be formed from any suitable monomer. In at least one aspect of the present invention, the hydrogel may be formed by free radical polymerization in the presence of water. Initiation of the formation of the hydrogel may be begun by ultra-violet curing with an initiator and a multifunctional cross-linking agent. While only one initiator is necessary, the hydrogel precursors may contain one or more second initiators. The initiators can be photo-initiators or chemical initiators such as those activated by heat or by reduction/oxidation (redox) reactions.

While any suitable monomer is contemplated by the present invention, exemplary functional monomers include: N-vinyl pyrrolidone (NVP), hydroxyethyl methacrylate (HEMA), methacrylic acid (MA) or its salt, styrene sulfonic acid (SSA) or its salt, potassium sulfopropyl acrylate (KPSA), dimethyl acrylamide (DMA), dimethyl amino ethyl methacrylate (DMAEMA) or its quaternary salt derivative, acrylamido methyl propane sulfonic acid (AMPS) or its salt, and the combination of any of the above. Additionally, the acid and salt of an exemplary functional monomer may be included in the hydrogel. Desirably, the hydrogels of the present invention are made from various classes of monomers including acrylates, vinyls, amides, esters, etc, of which can be electrically neutral, cationic or anionic. Combination of functional monomers also is possible to achieve desired physical, chemical mechanical and electrical properties. Compared to prior hydrogels, the hydrogels of the present invention hydrate the skin's surface more effectively and lower the skin's electrical resistance resulting in lower generation of heat and lower incidence of burning upon electrical stimulation. In addition, the present hydrogels more effectively wet around skin hair and, consequently, more sufficiently contact a subject's skin resulting in increased efficacy in procedures such as defibrillation as well as reduced heating and burning of skin surfaces and, generally require no preparation of the skin surface prior to use. Further, the present hydrogels are self-preserving and are resistant to degradation because of the compatibility of the monomer with the other ingredients present in the hydrogel.

Generally speaking, the monomer is desirably between about 10 to about 80% by weight of the composition, more desirably between about 40 to about 75% by weight of the composition, and even more desirably between about 50 to about 75% by weight of the composition.

Examples of specific desirable cationic acrylates are: acryloyloxyethyltrimethyl ammonium chloride which is readily available from CPS Chemical Co. (New Jersey) or Allied Colloid (U.K.); acryloyloxyethyltrimethyl ammonium methyl sulfate which is also available from CPS Chemical Co. or Allied Colloid; and, acrylamidopropyltrimethyl ammonium chloride, which is available from Stockhausen (Germany). The desired process for making hydrogels with these exemplary acrylates is described in detail below.

A cationic acrylate hydrogel suitable for the present invention will generally be somewhat clear in color, viscous, and tacky to the touch. The hydrogel tends to be sufficiently adhesive to a subject's skin, yet sufficiently cohesive to be easily removable from the subject's skin and separable from itself. As noted above, the hydrogels suitable for the present invention can be formed by in-situ free radical polymerization of a water soluble monomer in the presence of water, desirably by ultra-violet curing with at least one initiator, multi-functional cross-linking agent(s), and a solvent. For example, an appropriate acrylate monomer, water, electrolyte (e.g. sodium sulfate), initiator or catalyst (e.g., 1-hydroxycyclohexylphenol ketone, etc.), multi-functional cross-linker (e.g., methylene-bis-acrylamide, etc.), and solvent (e.g., dimethyl sulfoxide.) are combined, placed in a mold, and exposed to an appropriate amount of ultra-violet radiation.

Examples of co-monomers which may be used with the present invention include co-monomers soluble in water and, even more desirably, include anionic co-monomers. The amount of co-monomer to be used may be in the range of about 5 to about 50% by weight, desirably about 10 to about 30% by weight, based on the amount of reactants used. Examples of suitable co-monomers include: unsaturated organic carboxylic acids such as acrylic acid, methacrylic acid, maleic acid, itaconic acid, and citraconic acid and salts thereof, unsaturated organic sulfonic acids such as styrene sulfonic acid, methallyl sulfonic acid, 2-sulfoethyl acrylate, 2-sulfoethyl methacrylate, 3-sulfopropyl acrylate, 3-sulfopropyl methacrylate, acrylamido-methylpropane sulfonic acid and salts thereof, N,N-dimethylacrylamide, vinyl acetate, other radically polymerizable ionic monomers containing a carbon-carbon double bond, and non-N-vinyl lactam co-monomers useful with N-vinyl lactam monomeric units such as N-vinyl-2-pyrrolidone, N-vinyl-2-valerolactam, N-vinyl-2-caprolactam, and mixtures thereof. Among the ionic monomers enumerated above, particularly desirable selections are 3-sulfopropylacrylate or methacrylate, and salts thereof. Examples of cations involved in the formation of such salts include sodium, potassium, lithium, and ammonium ions. Ionic monomers may be used singly or in a mixture of two or more monomers.

Any suitable organic solvent may be used. The desirability of a specific organic solvent and/or the amount thereof may vary or depend in part on the other components and quantities thereof selected to make up the hydrogel precursor. The use of any organic solvent capable of dissolving the initiator up to an amount equal to the initiator's solubility limit is desired. Suitable organic solvents include, but are not limited to, dimethyl sulfoxide and glycerine.

The organic solvent is adapted to dissolve the initiator (hydrophobic or hydrophilic) and is water soluble. The organic solvent is adapted to dissolve hydrophobic additives such as lipids, anti-oxidants, drugs, and fragrances. Additionally, the organic solvent is adapted to dissolve skin health agents such as aloe Vera, glycerin, vitamin E, vitamin B, provitamin B, vitamin E acetate, or chitosan.

It is contemplated that a organic solvent may be present in a positive amount up to about 20% by weight of the hydrogel precursor and, more desirably, between about 0.5% to about 5% by weight of the hydrogel precursor.

Present hydrogels may include an optional buffer system to help control the pH, prevent discoloration, and/or prevent breakdown due to an extended presence of water (i.e., hydrolysis). The use of a buffer system with the present hydrogel is desired to provide the hydrogel with a commercially suitable shelf-life (i.e., a shelf-life of over one year) without discoloration. Suitable buffers include, but are not limited to, conventional buffers such as sodium hydroxide, sodium potassium tartarate, and/or sodium phosphate monobasic, all of which are commercially readily available from Aldrich Chemical Co., Inc., Milwaukee, Wis.

In addition, the use of buffers also helps to prevent electrochemical burning of a subject by helping to prevent pH changes and/or shifts as a current is driven through a pair of hydrogel electrodes. Typically, in prior systems, as current is driven through a pair of hydrogel electrodes, one electrode becomes more acidic (i.e., its pH decreases) while the other electrode becomes more basic (i.e., its pH increases). This pH shifting problem is particularly prevalent if current is driven through such electrodes for a long period of time (e.g., over 1 hour), such as during a procedure wherein a patient's heart is being paced. The desired use of a buffer system as is suggested in the present invention helps safeguard against such pH changes as current is driven therethrough and thereby enables use of the electrodes made from the present hydrogel for longer periods (e.g., over 24 hours) without electrochemical burning.

Therefore, it is desired that buffer (or a suitable alternative as described below) be included to stabilize the resulting polymer, to avoid hydrolysis of the hydrogel, and to avoid pH shifts due to the passage of direct current through the hydrogel. Buffers help both to reduce or prevent corrosion of metal conductors and also are conductivity enhancers themselves. Some buffers prevent undesirable yellowing of the hydrogel. The present hydrogel may include sufficient buffer to maintain the pH of the hydrogel in a range of about 3 to about 8.5, and more desirably about 5.5 to about 7, but the pH may be adjusted as desired. In most aspects of the present invention, a buffer may be present in the hydrogel precursor in an amount up to about 10% by weight, and more desirably from about 0 to about 5% by weight of the hydrogel precursor.

As an alternative to the use of conventional buffers, an amount of the acidic form of the monomer used may be used in the hydrogel precursor to adjust the pH of the hydrogel. Desirably, an amount of the acidic form of the monomer will be combined with the salt of the monomer so that an additional conventional buffer may not be needed. In this regard, pH is conventionally adjusted in hydrogels by utilizing a dual buffer system including a non-monomeric acidic salt such as an aluminum potassium sulfate and an additional buffer having a pH greater than 7 such as sodium hydroxide. For example, conventionally, aluminum potassium sulfate, or another non-monomeric acidic salt, is added to the hydrogel precursor in an amount to stabilize the resulting polymer, however, the amount utilized may result in an unacceptable drop in pH. Because of this drop in pH, sodium hydroxide, or another buffer having a pH greater than 7, is added to the hydrogel precursor to bring the pH up to a satisfactory level.

This dual buffer system creates many potential problems such as buffer incompatibility with the monomer and formation of a substantial amount of precipitates in the hydrogel which may lead to a potential decrease in conductivity.

Additionally, an acidic salt may be used by itself, and not as part of a dual buffer system, to maintain the pH in the desired range.

However, utilizing the salt of the monomer in conjunction with the acid (as a pH adjuster) eliminates potential problems such as buffer incompatibility with the monomer while still increasing shelf life and stability of the monomer solution.

The present invention also contemplates the inclusion of other additives, such as conductivity enhancers, pharmaceuticals, humectants, plasticizers, skin health agents, and the like. These other additives may be included either before or after a curing step. The appropriateness of such additives is generally dependent upon the intended end use of the particular hydrogel.

Any suitable additive or combination of additives such as those suggested above is contemplated. The specific additive and/or the amount thereof which is included may vary or depend in part on the other components and quantities thereof selected to make up the hydrogel. Exemplary skin health agents and/or skin care ingredients include but are not limited to vitamins (e.g., B, D, E, E acetate, etc.), antioxidants, chitosan, aloe Vera, hyaluronic acid (HA), heparin, chondroitin sulfate, dextran sulfate, and collagen IV. Still other exemplary additives may include but are not limited to anti-inflammation agents, anti-oxidants, aesthetic agents (e.g., color dyes to alter appearance of the hydrogels), or fragrances.

Additionally, the skin health agent (i.e. chitosan glycolate, silk hydrolyzate, or polyvinylpyrrolidone) may be an electrically conductive layer which is in communication with the electrically conductive hydrogel. In this regard, the skin health agent may optionally not be present in the hydrogel but may act as a separate hypoallergenic layer in communication with the hydrogel in order to reduce skin irritation of the patient. Desirably, this separate hypoallergenic layer will not decrease the conductivity of the hydrogel.

Additionally, the use of suitable conductivity enhancer is contemplated. The specific enhancer and/or the amount thereof which is included in the hydrogel may vary or depend in part on the other components, and quantities thereof selected to make up the hydrogel. Exemplary conductivity enhancers include but are not limited to salts such as potassium chloride, sodium chloride, potassium sulfate, sodium sulfate and the like. These salts are desired inasmuch as human bodies use them for conduction. Additional examples of salts which may be appropriate are lithium chloride, lithium perchlorate, ammonium chloride, calcium chloride, and/or magnesium chloride. Other chloride salts, iodide salts, bromide salts, and/or halide salts also may be suitable.

Other salts, such as salts of weak organic acids or polymeric electrolytes may be desirable. These salts are compatible with human bodies and with the chemistry of the hydrogels of the present invention and may be used as conductivity enhancers where desired chloride salts might interfere (i.e., corrode) with aluminum and/or stainless steel metal components used to interface the hydrogel with medical equipment. Examples of salts which may be suitable include sodium citrate or magnesium acetate.

Although use of a conductivity enhancer is optional, the amount of conductivity enhancer in a hydrogel of the present invention is desirably in the range of none to an amount which will enhance the conductivity of the hydrogel. For example, if a conductivity enhancer is utilized, the conductivity enhancer may desirably be present in an amount between greater than about 0 (e.g., 0.01%) to about 15% by weight of the hydrogel precursor and, even more desirably, between greater than about 0 (e.g., 0.01%) to less than about 5% by weight of the hydrogel precursor.

The addition of conductivity enhancers may be desired even though the hydrogel of the present invention is a polyelectrolyte ionically disassociated in water and, therefore, conductive. In use, a lower specified quantity of polyelectrolyte (and thus a hydrogel having a correspondingly lower viscosity) may be desired in situations such as when the hydrogel must wet around chest hair. In such cases, the addition of a conductivity enhancer may be useful.

However, while the addition of a conductivity enhancer to a hydrogel or hydrogel precursor has generally been thought to provide for better electrical conductivity when compared to hydrogels without the added conductivity enhancer, it has been discovered that at least some aspects of the present invention which do not include an added conductivity enhancer demonstrate better "in use" conductivity as compared to those hydrogels which included a conductivity enhancer. For example, in certain instances, salts, despite being inherently electrically conductive because of their ionicity, may negatively yield undesirable effects such as the "salting out" effect which may result in phase separation and/or contribute to the reduced conductivity of certain formulations. This is especially true the longer the shelf life a hydrogel may be subjected to.

As indicated herein, an optional buffer and/or one or more of the optional polyelectrolyte additives (e.g., HA, chondroitin sulfate, phospholipids, etc.) may exhibit conductivity enhancing properties; however, the buffer and/or polyelectrolyte additives are not contemplated to be included in the determination of the amount of a conductivity enhancer in the hydrogel as the buffer and/or polyelectrolyte additives may not form a continuous path within the gel and between the gel and the skin.

As is mentioned above, initiators are used in the polymerization of the hydrogel precursors described herein. Examples of initiators which may be used include IRGACURE® 184 (1-hydroxycyclohexyl phenyl ketone), IRGACURE®. 2959 (4-(2-hydroxyethoxy)phenyl-(2-hydroxy-2-methylpropyl)ketone)), and DAROCURE® 1173.alpha.-hydroxy-.alpha.,.alpha.-dimethylacetophenone), all commercially available from Ciba Specialty Chemicals. These ultraviolet UV initiators are desired because they are non-yellowing. Other initiators which may maintain the desired water-white and water-clear appearance of the present hydrogels also are desired. Additional examples of suitable initiators (which may be photo initiators or thermal initiators) may include benzoyl peroxide, azo-bis-isobutyronitrile, di-t-butyl peroxide, bromyl peroxide, cumyl peroxide, lauroyl peroxide, isopropyl percarbonate, methylethyl ketone peroxide, cyclohexane peroxide, tutylhydroperoxide, di-t-amyl peroxide, dicumyl peroxide, t-butyl perbenzoate, benzoin alkyl ethers (such as benzoin, benzoin isopropyl ether, and benzoin isobutyl ether), benzophenones (such as benzophenone and methyl-o-benzoyl benzoate), actophenones (such as acetophenone, trichloroacetophenone, 2,2-diethoxyacetophenone, p-t-butyltrichloro-acetophenone, 2,2-dimethoxy-2-phenyl-acetophenone, and p-dimethylaminoacetophenone), thioxanthones (such as xanthone, thioxanthone, 2-chlorothioxanthone, and 2-isopropylthioxanthone), benzyl 2-ethyl anthraquinone, methylbenzoyl formate, 2-hydroxy-2-methyl-1-phenylpropane-1-one, 2-hydroxy-4'-isopropyl-2-methyl propiophenone, .alpha.-hydroxy ketone, tetramethyl thiuram monosulfide, allyl diazonium salt, and combinations of camphorquinone and ethyl 4-(N,N-dimethylamino)benzoate. Other suitable initiators may be found in, for example, Berner, et al., "Photo Initiators—An Overview", J. Radiation Curing (April 1979), pp. 2 9.

Although only one initiator is necessary, the hydrogel may contain one or more second initiators. The one or more second initiators can be photo or chemical initiators.

Where there is only one initiator, the amount of initiator is desirably within the range of about 0.01 to about 5% by weight of the hydrogel precursor, more desirably, within the range of about 0.05 to about 2% by weight of the hydrogel precursor and, even more desirably, within the range of about 0.1 to about 0.5% by weight of the hydrogel precursor. Where one or more second initiators are present, the amount of one or more second initiators is desirably within the range of about 0.01 to about 5% by weight of the hydrogel precursor, and more desirably within the range of about 0.05 to about 2% by weight of the hydrogel precursor and, even more desirably, within the range of about 0.1 to about 0.5% by weight of the hydrogel precursor. However, where multiple initiators are present, it is generally desirable that the combined amount of the initiators be about 5% or less by weight of the hydrogel precursor, and more desirably within the range of about 0.02 to about 5% by weight of the hydrogel precursor.

UV curing parameters to achieve desired polymer properties are well known to those skilled in the art. A photo initiator for the present purposes tends to operate by absorbing select wavelengths of UV to produce radical initiating species to induce monomer polymerization. The wavelengths and curing area set the style of UV bulb used in the curing process. Inhibition of polymerization due to dissolved oxygen, monomer inhibitors, or other radical scavenging moieties may be overcome by changing the power, by pulsing, and/or by using initiator accelerators.

It will be appreciated that each photo initiator is responsive to a specific or narrow wavelength range of UV light. At least one aspect of the present invention takes advantage of this property and incorporates two or more photo initiators in a hydrogel precursor. The addition of more than one initiator in a hydrogel precursor allows for a broader range of the energy or range of wavelengths emitted by a UV source to be utilized. The utilization of multiple initiators can further reduce solubility limit concerns and related compatibility concerns, as more efficient polymerization may be able to be achieved with two initiators present in a hydrogel precursor than with either of the initiators used alone at the same overall initiator concentration.

The synergistic effect of initiators has not been previously identified or exhibited in previous hydrogels which incorporated one photo initiator, if any initiator at all. It is further believed that the inclusion of initiators having different rates of initiation and/or the inclusion of initiators which begin initiation of polymerization of the monomer at different times relative to each other (such as that which may be experienced by multiple initiators (e.g., a thermally activated chemical initiator (TACI) and a photo initiator)) contributes to a higher yielding polymerization. That is, for example, where two photo initiators are included, one may have a lower UV wavelength trigger and may be more energetic (providing for a faster rate of initiation and reaction) than the other initiator which is triggered by a higher UV wavelength or range. The faster initiator may also die or be consumed faster than the other. It is contemplated that it may be advantageous to have polymerization occur at different rates and/or at a mixed rate which may not be obtainable with one initiator or with an initiator which is suitable for a particular hydrogel precursor. An example of initiators which are not triggered or activated simultaneously, may be found in the present invention where a photo initiator and a TACI are in a hydrogel precursor, and the photo initiator is triggered by a UV source and reacts with the monomers in the precursor so as to generate heat to trigger the TACI.

While numerous combinations and variations of initiators are possible, it is believed that the combination of multiple initiators provides more favorable kinetics which affords a higher probability of more extensive polymerization of the monomer and/or other monomeric residues.

It is a further discovery of the present invention that a TACI may be included to take advantage of the benefits of multiple initiator polymerization. As some heat is necessary to trigger a TACI, it is contemplated that a TACI will generally be included only where heat will be present in or produced in the hydrogel precursor in a sufficient amount to trigger the TACI. As radical polymerization reactions induced by photo initiators are known to be exothermic and thus to generate heat in response to UV exposure, at least one aspect of the present invention is directed to the inclusion of a TACI in a hydrogel precursor where a photo initiator is also present so as to allow the TACI to take advantage of the heat generated by the radical polymerization reaction induced by a photo initiator. It is also contemplated that a TACI can be included where multiple photo initiators are present. The presence of multiple photo initiators provides for the potential benefits of multiple initiators discussed above yet also provides for the triggering of a TACI where the heat generated by one photo initiator may be insufficient to trigger or fully trigger the TACI (depending on the photo initiators and the TACI involved), whereby the TACI can further promote or complete the polymerization of the functional monomer and other monomeric residues in a hydrogel precursor. Multiple TACIs are also contemplated.

It is believed that literature reports and/or clinical experience lack any report or descriptions of utilizing the combination of one or more photo initiators and a TACI in order to obtain the more complete polymerization of a hydrogel precursor, thereby leading to a more stable, less malodorous, and/or less skin irritating hydrogel.

As is also noted above, cross-linking agents are desirably used to cross-link the present hydrogels. Examples of multifunctional cross-linking agents which may be used include, for example, methylene-bis-acrylamide and diethylene glycol diacrylate which are both commercially available from Polysciences, Inc., Warrington, Pa. Additional examples of cross-linking agents which may be satisfactory for use in the present invention include: poly(ethylene glycol) diacrylate, triethylene glycol-bis-methacrylate, ethylene glycol-bis-methacrylate, ethylene glycol-dimethacrylate, bisacrylamide, triethyleneglycol-bis-acrylate, 3,3'-ethylidene-bis(N-vinyl-2-pyrrolidone), trimethylolpropate trimethacrylate, glycerol trimethacrylate, polyethylene glycol dimethacrylate, and other multifunctional polyacrylate and polymethacrylate crosslinkers.

The amount of cross-linking agent is desirably within the range of about 0.01 to about 2% by weight of the hydrogel precursor and, more desirably, within the range of about 0.05 to about 0.5% by weight of the hydrogel precursor.

We will now turn to specific exemplary embodiments of hydrogels of the present invention. Two sets of examples with a number of exemplary formulas are provided below. In each of the Formulas, the starting materials were mixed in the order given below and placed under a Fusion Systems 600 Watt Continuous UV Lamp available from Fusion UV Systems, Inc., Woburn, Mass. The UV lamp was a F600S Ultra-violet Lamp System and it was used at a dose of about 5.084 $J/cm^2$.

EXAMPLES

The following examples are displayed in order to enable one of ordinary skill in the art to practice the claimed invention, but the examples are not to be construed as limiting the scope of the invention, which is defined by the claims and all equivalents thereto.

Example 1

The purpose of Example 1 is to compare levels of conductivity between hydrogel samples utilizing a dual buffer system and hydrogels utilizing one buffer.

The sample ingredients were mixed in the order detailed below using conventional mixing techniques. Actual weight percentages of the deionized water and the neat form of the other ingredients are presented in a table following each individual comparative sample or sample.

Comparative Sample 1 (Control)
  23.99% deionized (DI) Water
  0.0% sodium sulfate 71.00% Monomer (N,N-Dimethylaminoethyl acrylate dimethyl sulfate quaternary available from Ciba Specialty Chemicals, Tarrytown, N.Y., under the tradename AGE-FLEX® FA1Q80DMS)

0.1% Cross-linking Agent (Methylene-Bis-Acrylamide (available from Aldrich)

3.11% [dimethyl sulfoxide (97%) (Organic Solvent) and Photo initiator (3%)(IRGACURE® 184) combined], both available from Ciba Specialty Chemicals 1.00% Aluminum Potassium Sulfate 0.80% of 50% Sodium Hydroxide Solution

TABLE 1

(Comparative Sample 1)

| Ingredient | Weight Percent |
|---|---|
| deionized (DI) Water | 23.99 |
| sodium sulfate | 0.00 |
| Monomer | 71.00 |
| Cross-linking Agent | 0.10 |
| dimethyl sulfoxide | 3.00 |
| Photo initiator | 0.11 |
| Aluminum Potassium Sulfate | 1.00 |
| Sodium Hydroxide Solution | 0.40 |

Comparative Sample 2

16.89% DI Water 0.0% sodium sulfate

10% of Cross-linking Agent (1% solution of Methylene-Bis-Acrylamide (available from Aldrich)

60.00% Monomer (salt form of acrylamido methyl propane sulfonic acid available from Lubrizol under the trade name AMPS 2405)

3.11% [dimethyl sulfoxide (97%) (Organic Solvent) and Photo initiator (3%)(IRGACURE® 184) combined], both available from Ciba Specialty Chemicals 10.00% of 10% Aluminum Potassium Sulfate Solution 0.40% of 50% Sodium Hydroxide Solution

TABLE 2

(Comparative Sample 2)

| Ingredient | Weight Percent |
|---|---|
| deionized (DI) Water | 16.89 |
| sodium sulfate | 0.00 |
| Monomer | 60.00 |
| Cross-linking Agent | 0.10 |
| dimethyl sulfoxide | 3.00 |
| Photo initiator | 0.11 |
| Aluminum Potassium Sulfate Solution | 1.00 |
| Sodium Hydroxide Solution | 0.20 |

Sample 1

27.90% DI Water 0.0% sodium sulfate

10% of Cross-linking Agent (1% solution of Methylene-Bis-Acrylamide (available from Aldrich)

60.00% Monomer (salt form of acrylamido methyl propane sulfonic acid available from Lubrizol under the trade name AMPS 2405)

2.10% [dimethyl sulfoxide (97%) (Organic Solvent) and Photo initiator (3%)(IRGACURE® 184) combined], both available from Ciba Specialty Chemicals 0.06% of 10% Aluminum Potassium Sulfate Solution 0.00% of 50% Sodium Hydroxide Solution

TABLE 3

(Sample 1)

| Ingredient | Weight Percent |
|---|---|
| deionized (DI) Water | 27.900 |
| sodium sulfate | 0.000 |
| Cross-linking Agent | 0.100 |
| Monomer | 60.000 |
| dimethyl sulfoxide | 2.037 |
| Photo initiator | 0.063 |
| Aluminum Potassium Sulfate Solution | 0.006 |
| Sodium Hydroxide Solution | 0.000 |

Sample 2

16.89% DI Water 10.0% of 20% sodium sulfate

10% of Cross-linking Agent (1% solution of Methylene-Bis-Acrylamide (available from Aldrich)

60.00% Monomer (salt form of acrylamido methyl propane sulfonic acid available from Lubrizol under the trade name AMPS 2405)

2.10% [dimethyl sulfoxide (97%) (Organic Solvent) and Photo initiator (3%)(IRGACURE® 184) combined], both available from Ciba Specialty Chemicals 0.06% of 10% Aluminum Potassium Sulfate Solution 0.00% of 50% Sodium Hydroxide Solution

TABLE 4

(Sample 2)

| Ingredient | Weight Percent |
|---|---|
| deionized (DI) Water | 16.890 |
| sodium sulfate | 2.000 |
| Cross-linking Agent | 0.100 |
| Monomer | 60.000 |
| dimethyl sulfoxide | 2.037 |
| Photo initiator | 0.063 |
| Aluminum Potassium Sulfate Solution | 0.006 |
| Sodium Hydroxide Solution | 0.000 |

Sample 3

11.89% DI Water 15.0% of 20% sodium sulfate

10% of Cross-linking Agent (1% solution of Methylene-Bis-Acrylamide (available from Aldrich)

60.00% Monomer (salt form of acrylamido methyl propane sulfonic acid available from Lubrizol under the trade name AMPS 2405)

3.110% [dimethyl sulfoxide (97%) (Organic Solvent) and Photo initiator (3%)(IRGACURE® 184) combined], both available from Ciba Specialty Chemicals 0.06% of 10% Aluminum Potassium Sulfate Solution

TABLE 6

(Sample 3)

| Ingredient | Weight Percent |
|---|---|
| deionized (DI) Water | 11.890 |
| sodium sulfate | 3.000 |
| Cross-linking Agent | 0.100 |
| Monomer | 60.000 |
| dimethyl sulfoxide | 3.017 |

TABLE 6-continued (Sample 3)

| Ingredient | Weight Percent |
|---|---|
| Photo initiator | 0.093 |
| Aluminum Potassium Sulfate Solution | 0.006 |
| Sodium Hydroxide Solution | 0.000 |

The pH and Conductivity of the samples were measured utilizing an Orion 4 Star pH and Conductivity Portable Multimeter equipped with an orion 013005 MB conductivity cell and an Orion 9145 BN pH probe. This equipment is available from Thermo Electron Corporation.

The results of the conductivity and pH measurements for comparative samples 1 and 2 and samples 1 through 3 are presented in table 7 below.

TABLE 7

| Formula | Wt % Na2SO4 | Conductivity | pH |
|---|---|---|---|
| Comparative Sample 1 (Control) | 0 | 40.5 | 5.18 |
| Comparative Sample 2 | 0 | 32.6 | 6.15 |
| Sample 1 | 0 | 32.0 | 7.35 |
| Sample 2 | 10 | 35.7 | 6.88 |
| Sample 3 | 15 | 36.5 | 6.95 |

As can be seen from Table 7, satisfactory levels of conductivity and pH may be maintained when the conventional dual buffer system is not utilized. The samples utilized only a non-monomeric acidic salt as a buffer (Aluminum potassium sulfate), and did not utilize Sodium Hydroxide or another buffer having a pH greater than 7.

Example 2

The purpose of example 2 is to compare levels of conductivity between hydrogel samples utilizing a dual buffer system and hydrogels utilizing the acidic form of a monomer to adjust the pH of the hydrogel sample.

The sample ingredients were mixed in the order detailed below using conventional mixing techniques. Actual weight percentages of the deionized water and the neat form of the other ingredients are presented in a table following each individual comparative sample or sample.

Comparative Sample 1 (Control)
  23.99% DI Water
  0.0% sodium sulfate
  71.00% Monomer (N,N-Dimethylaminoethyl acrylate dimethyl sulfate quaternary available from Ciba Specialty Chemicals under the tradename AGEFLEX® FA1Q80DMS)
  0.1% Cross-linking Agent (Methylene-Bis-Acrylamide (available from Aldrich)
  3.11% [dimethyl sulfoxide (97%) (Organic Solvent) and Photo initiator (3%)(IRGACURE® 184) combined], both available from Ciba Specialty Chemicals
  1.00% Aluminum Potassium Sulfate
  0.80% of 50% Sodium Hydroxide Solution

TABLE 1

(Comparative Sample 1)

| Ingredient | Weight Percent |
|---|---|
| deionized (DI) Water | 11.890 |
| sodium sulfate | 0.000 |
| Monomer | 71.000 |
| Cross-linking agent | 0.100 |
| dimethyl sulfoxide | 3.017 |
| Photo initiator | 0.093 |
| Aluminum Potassium Sulfate | 1.000 |
| Sodium Hydroxide Solution | 0.800 |

Sample 1
  60.00% Monomer (salt form of acrylamido methyl propane sulfonic acid available from Lubrizol under the trade name AMPS 2405
  0.005% Monomer (acid form of acrylamido methyl propane sulfonic acid available from Lubrizol under the trade name AMPS 2405
  17.895% DI Water
  10.0% Cross-linking Agent (1% solution of Methylene-Bis-Acrylamide (available from Aldrich)
  10.0% of 20% sodium sulfate
  2.10% [dimethyl sulfoxide (97%) (Organic Solvent) and Photo initiator (3%)(IRGACURE® 184)] combined, both available from Ciba Specialty Chemicals

TABLE 2

(Sample 1)

| Ingredient | Weight Percent |
|---|---|
| Salt form of monomer | 60.000 |
| Acid form of monomer | 0.005 |
| Deionized water | 17.895 |
| Cross-linking agent | 0.100 |
| Sodium sulfate | 2.000 |
| Dimethyl sulfoxide | 2.037 |
| initiator | 0.063 |
| Sodium hydroxide solution | 0.000 |

Sample 2
  60.00% Monomer (salt form of acrylamido methyl propane sulfonic acid available from Lubrizol under the trade name AMPS 2405
  0.005% Monomer (acid form of acrylamido methyl propane sulfonic acid available from Lubrizol under the trade name AMPS 2405
  12.895% DI Water
  10.0% Cross-linking Agent (1% solution of Methylene-Bis-Acrylamide (available from Aldrich)
  15.0% of 20% sodium sulfate
  2.10% [dimethyl sulfoxide (97%) (Organic Solvent) and Photo initiator (3%)(IRGACURE® 184) combined], both available from Ciba Specialty Chemicals

TABLE 3

(Sample 2)

| Ingredient | Weight Percent |
|---|---|
| Salt form of monomer | 60.000 |
| Acid form of monomer | 0.005 |
| Deionized water | 12.950 |
| Cross-linking agent | 0.100 |

TABLE 3-continued (Sample 2)

| Ingredient | Weight Percent |
| --- | --- |
| Sodium sulfate | 3.000 |
| Dimethyl sulfoxide | 2.037 |
| initiator | 0.063 |
| Sodium hydroxide solution | 0.000 |

The results of the conductivity and pH measurements for comparative sample 1 and samples 1 and 2 are presented in table 4 below.

TABLE 4

| Formula | Wt % Na2SO4 | Conductivity | pH |
| --- | --- | --- | --- |
| Formula 1 (Control) | 0 | 40.5 | 5.18 |
| Formula 2 | 10 | 35.5 | 8.11 |
| Formula 3 | 15 | 36.7 | 8.30 |

As can be seen in Table 4, satisfactory conductivity may be achieved without the use of the dual buffer system found in the control formulation. The samples in Example 4 contain the salt form of the monomer and achieve pH adjustment by utilizing the acid form of the monomer without the utilization of a dual buffer system such as aluminum potassium sulfate/sodium hydroxide.

It will be appreciated that the Exemplary formulations were substantially free of precipitates and did not exude odor indicative of a substantial amount of acrylic acid residue. In this regard, the lack of odor in the formulations indicate complete or near complete polymerization of the monomer and also indicate that the hydrogel is not susceptible to irritating the skin.

It is of note that the exemplary formulations further distinguish themselves from prior hydrogels by utilizing an organic solvent rather than a solubilizer for the initiator. The organic solvent contributes to effective hydrogel formulations without the added substantial costs of a solubilizer.

In summary, it has been discovered that the hydrogel precursors of the present invention provide for a hydrogel which provide for a reduction in odor and skin irritation to the patient as compared to prior hydrogels. The novel formulations provide the ability of using the hydrogel or devices incorporating the hydrogel (e.g., electrodes) for longer periods of time without concern or with reduced concern for skin irritation and/or malodor. The formulations of the present invention desirably provide or are directed to at least one of the following: a more efficient polymerization process, a synergistic initiation system (or at least one which has a synergistic effect) including UV-activated initiators (photoinitiator) and/or heat-activated initiators, a polymerizing monomer solution that includes solubilizing agents to improve the homogeneity of the polymerizing solution, complexing agents to lower the volatility of volatile compounds, and skin care ingredients that could protect skin against undesirable elements. Additionally, the hydrogel provides for complete or near complete polymerization of the monomer without the use of a solubilizer.

It should be noted that while the above specific examples show particular desired embodiments of the present invention, substitution of the specific constituents of those examples with materials as disclosed herein and as are known in the art may be made without departing from the scope of the present invention. Thus, while different aspects of the present invention have been shown and described, various modifications may be made without departing from the scope of the present invention, and all such modifications and equivalents are intended to be covered.

The invention claimed is:

1. A substantially precipitate free electrically conductive hydrogel formed from a composition comprising:
   a monomer;
   at least one initiator;
   a cross-linking agent; and
   an organic solvent,
   wherein the composition does not comprise a dual buffer system, the pH of the electrically conductive hydrogel is maintained in the range of 3 to 8.5 in the absence of the dual buffer system and wherein the composition does not comprise a solubilizer for the at least one initiator.

2. The hydrogel of claim 1, wherein the pH is maintained in the range of 3 to 8.5 by the addition of an acidic salt.

3. The hydrogel of claim 1, wherein the pH is maintained in the range of 3 to 8.5 by the addition of the acid form of the monomer.

4. The hydrogel of claim 1, wherein the organic solvent is dimethyl sulfoxide.

5. The hydrogel of claim 1, wherein the monomer is in the salt form.

6. The hydrogel of claim 1, wherein the organic solvent comprises between about 0.5% and about 5% by weight of the composition.

7. The hydrogel of claim 1 the conductive hydrogel is formed from a composition that further comprises a buffer.

8. The hydrogel of claim 1 wherein the monomer comprises about 10% to about 80% by weight of the composition.

9. The hydrogel of claim 8 wherein the monomer comprises about 40% to about 75% by weight of the composition.

10. The hydrogel of claim 1 wherein the at least one initiator comprises about 0.01% to about 2% by weight of the composition.

11. The hydrogel of claim 1 wherein the cross-linking agent comprises about 0.01% to about 2% by weight of the composition.

12. The hydrogel of claim 1 wherein the monomer is N,N-Dimethylaminoethyl acrylate dimethyl sulfate quaternary, dimethyl amino ethyl methacrylate, acrylamido methyl propane sulfonic acid, or their salts.

13. The hydrogel of claim 1 wherein the at least one initiator comprises at least one chemical initiator, at least one photo initiator, or both.

14. The hydrogel of claim 13 wherein the at least one initiator is a thermally activated chemical initiator.

15. The hydrogel of claim 14 wherein the thermally activated chemical initiator is a disulfide based, peroxide based, or persulfate based initiator.

16. The hydrogel of claim 14 wherein the thermally activated chemical initiator is sodium metabisulfite.

17. The hydrogel of claim 1 wherein the at least one initiator is a hydrophobic initiator.

18. The hydrogel of claim 1, wherein the conductive hydrogel is formed from a composition that further comprises at least one conductivity enhancer, and wherein at most one conductivity enhancer is a buffer.

19. The hydrogel of claim 1 wherein the conductive hydrogel is formed from a composition that further comprises a skin health agent.

20. The hydrogel of claim 19 wherein the skin health agent is aloe vera, glycerin, vitamin E, vitamin B, provitamin B, vitamin E acetate, chitosan, or silk hydrolyzate.

21. An electrode comprising an electrically conductive adhesive hydrogel formed from a composition comprising:
- at least one monomer;
- at least one initiator;
- a cross-linking agent; and
- an organic solvent,
- wherein the composition does not comprise a dual buffer system, the pH of the electrically conductive hydrogel is maintained in the range of 3 to 8.5 in the absence of the dual buffer system and wherein the conductive hydrogel does not comprise a solubilizer for the at least one initiator.

22. The electrode of claim 21, further comprising a skin health agent which comprises an electrically conductive hypoallergenic layer which is in communication with the electrically conductive hydrogel.

23. The electrode of claim 22, wherein the skin health agent is aloe vera, glycerin, vitamin E, vitamin B, provitamin B, vitamin E acetate, chitosan, or silk hydrolyzate.

24. The electrode of claim 21 wherein the organic solvent is between about 0.5% and about 5% by weight of the composition.

25. The electrode of claim 21 wherein the at least one monomer comprises about 10% to about 80% by weight of the composition.

26. The composition of claim 25 wherein the at least one monomer comprises about 40% to about 75% by weight of the composition.

27. The composition of claim 21 wherein the at least one initiator comprises about 0.01% to about 2% by weight of the composition.

28. The composition of claim 21 wherein the cross-linking agent comprises about 0.01% to about 2% by weight of the composition.

29. The composition of claim 21 wherein the monomer is N,N-Dimethylaminoethyl acrylate dimethyl sulfate quaternary, dimethyl amino ethyl methacrylate, acrylamido methyl propane sulfonic acid or their salts.

30. The composition of claim 21, wherein the organic solvent is dimethyl sulfoxide.

31. The composition of claim 21, wherein the composition further comprises a conductivity enhancer.

32. A composition for an electrically conductive hydrogel comprising:
- at least one monomer;
- at least one initiator;
- a cross-linking agent; and
- an organic solvent selected from dimethyl sulfoxide,
- wherein the composition does not comprise a dual buffer system, the composition is adapted to form a hydrogel having a pH in the range of 3 to 8.5 in the absence of the dual buffer system and wherein the electrically conductive hydrogel does not comprise a solubilizer for the at least one initiator.

* * * * *